United States Patent [19]

Holtman

[11] Patent Number: 4,578,070
[45] Date of Patent: Mar. 25, 1986

[54] ABSORBENT STRUCTURE CONTAINING CORRUGATED WEB LAYERS

[75] Inventor: Dennis C. Holtman, Flemington, N.J.

[73] Assignee: Personal Products Company, Milltown, N.J.

[21] Appl. No.: 523,473

[22] Filed: Aug. 15, 1983

[51] Int. Cl.$^4$ ............................................. A61F 13/16
[52] U.S. Cl. .................................. 604/378; 604/372; 604/385 R; 604/379
[58] Field of Search ............... 604/379, 380, 360, 366, 604/374, 378, 385

[56] References Cited

U.S. PATENT DOCUMENTS 3,525,337 8/1970 Simons et al. ...................... 604/374

Primary Examiner—C. Fred Rosenbaum
Assistant Examiner—Sherri E. Vinyard
Attorney, Agent, or Firm—Martha A. Michaels

[57] ABSTRACT

An absorbent product is provided having a first fibrous layer in the form of a nonwoven web and a second layer which is discrete from the first layer but united to the first layer. The second layer has a higher capillary pressure than the first layer to provide preferential attraction and wicking of liquid. The layers are corrugated and stabilized to retain the transverse folds when wet.

17 Claims, 9 Drawing Figures

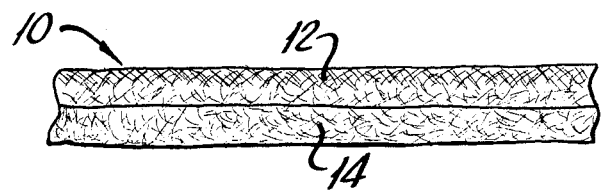
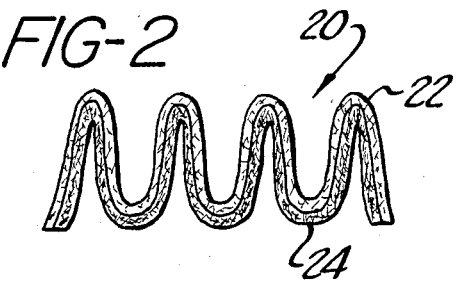
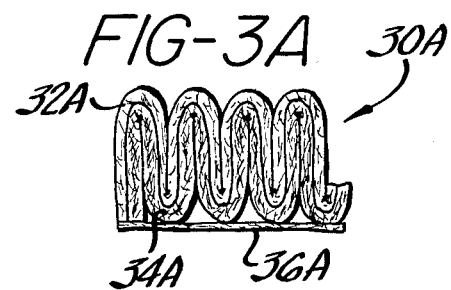
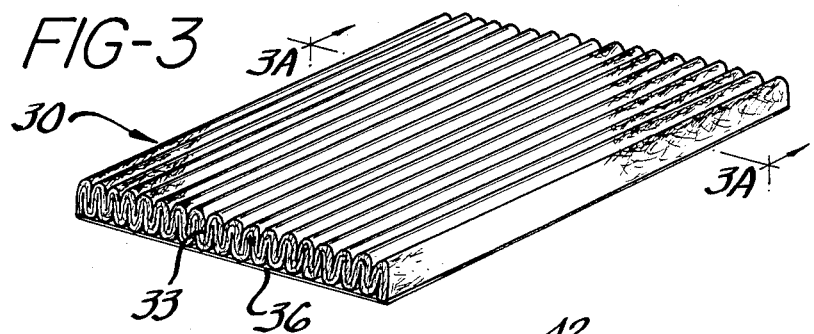
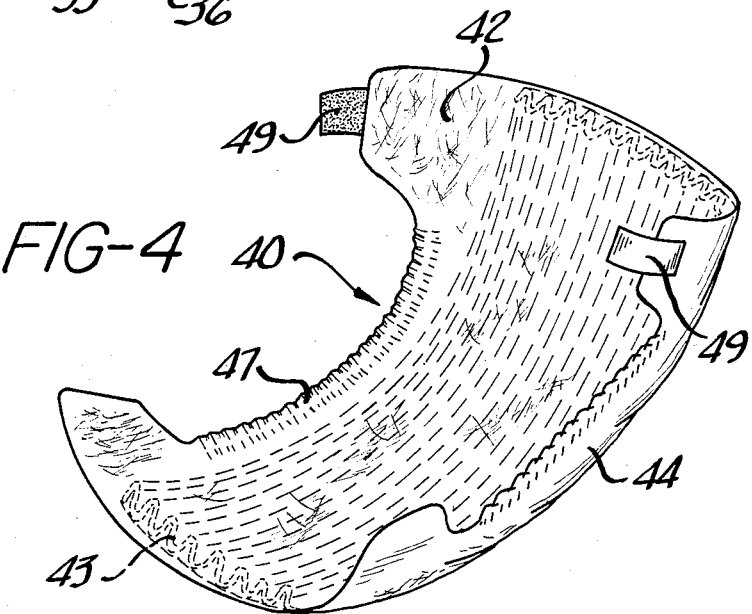

ABSORBENT STRUCTURE CONTAINING CORRUGATED WEB LAYERS

BACKGROUND OF THE INVENTION

The present invention relates to new and improved absorbent structures and, more particularly, to new and improved absorbent structures incorporating therein corrugated web layers.

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially in many of these products, especially diapers and sanitary napkins, the absorbent batt comprised what is termed "wadding" or plies of tissue. The wadding was disposed between an impermeable backing and a permeable facing and the plies of tissue were used to absorb and hopefully contain the liquid within the product. A diaper which utilizes such an absorbent batt is disclosed in U.S. Pat. No. Re. 26,151.

The wadding type of batt was replaced, for the most part, by an improved absorbent batt which comprises what is termed "fluffed wood pulp fibers". This absorbent batt comprises a layer of individualized wood pulp fibers with the layer having substantial thickness. A diaper which incorporates such a fluffed wood pulp absorbent batt is described in U.S. Pat. No. 2,788,003. This diaper had improved absorbent capacity and somewhat better containment than a diaper using a wadding layer. Also, the fluffed wood pulp layer is quite soft, flexible and conformable, and hence produces an improved diaper over diapers using wadding as the absorbent layer.

Though the fluffed wood pulp absorbent batts have improved capacity, the efficiency with which the capacity is used in a diaper or sanitary napkin is poor. The reason for this is that the fluid to be absorbed is generally deposited in a localized area within the absorbent batt and the ability of the fluid to move along the plane of the batt is poor. The fluid tends to follow a radial wicking path and consequently moves to the closest edge of the batt where it generally is no longer contained and the product leaks.

U.S. Pat. No. 3,017,304 discloses an absorbent product which incorporates in the product a densified paperlike layer. This paper-like layer acts as a wick, i.e., liquid which is placed on the layer tends to move rapidly along the plane of the layer. When incorporated in combination with fluffed wood pulp fiber, the resultant product uses the absorbent capacity of the fluffed wood pulp much more efficiently. Diapers which incorporate this paper-like layer combined with fluffed wood pulp are disclosed and described in U.S. Pat. Nos. 3,612,055 and 3,938,522. This concept of combining wicking ability, or a capillary skin or layer, with fluffed wood pulp fibers has gained wide acceptance in many absorbent products, including disposable diapers and sanitary napkins. Even though these products make much greater use of the capacity of the absorbent batt, they still do not totally contain the absorbed liquid. It is probable that these products will leak before the full capacity of the batt is used for absorption or at the very least before the entire liquid void by the user is absorbed. This is especially true when pressure is placed on the batt while wet. For example, a baby sitting down on a previously wetted diaper will very often cause the batt to leak.

A incontinent adult faces many problems. First, the void of an adult generally is much higher in volume than that of an infant. Second, a bulge under clothing is accepted by society for an infant, but the ambulatory adult with an incontinence problem longs for a product which is not visible through ordinary clothing. Third, the proportions and shape of the legs and torso of the adult differs considerably from those of an infant. Therefore, a mere enlargement of an infant diaper, such as that shown in U.S. Pat. No. 4,253,461, is not a satisfactory product.

In both the infant diaper and adult incontinent product marketplace, a product is needed which has a large storage capacity. For instance, shaped containers have been suggested. However, these containers have been substantially rigid, do not stay in place and are quite uncomfortable. A product with a substantially large liquid storage capacity, with an ability to move liquid away from the void zone, which is disposable, which is comfortable, and which does not show through wearing apparel is needed in the marketplace.

The present invention provides a new and improved absorbent product which provides a large storage capacity and ability to transport liquid from the void zone, which is soft and comfortable, and which can be designed so as not to be apparent through normal clothing. In addition, the new absorbent product will contain absorbed liquid even when pressure is placed upon the product during use.

SUMMARY OF THE INVENTION

The present invention provides a disposable absorbent product comprising a first fibrous layer in the form of a nonwoven web. A second fibrous layer discrete from the first layer but united to the first layer is provided which second layer has a higher capillary pressure than the first layer. This provides preferential wicking of liquid in the second layer. These layers, in their united form, are transversely folded to provide a corrugated structure which is stabilized in such a way as to retain its transverse folds even when wet. The absorbent product is generally stabilized on one side of the product, i.e., over the surface at the peaks of the transverse folds or in corrugations on one side thereof.

The first fibrous layer comprises substantially hydrophobic, resilient, preferably synthetic fibers in the form of a nonwoven web. The second layer is comprised of fibers (or in the case of peat moss, particles) which when placed in the form of a layer provides a higher capillary pressure than the capillary pressure of the first fibrous layer. As a result, the second layer drains liquid from the first layer and wicks the liquid away from the void zone.

In a preferred embodiment, the first fibrous layer is prepared in the form of a nonwoven web and the second layer is deposited by known procedures onto the first layer. The second layer is comprised of a wicking substance which provides a higher capillary pressure than that of the first layer. The wicking substance includes hydrophilic fibers such as cellulosic fibers, rayon fibers and other wicking substances such as peat moss or mixtures thereof or acrylic fibers or the like. The wicking substance which forms the second layer generally is comprised of fibers or particles in closely spaced relationship to promote the movement of liquid along the second layer.

When the absorbent product is utilized after the transverse folding or corrugation takes place, the liquid preferentially moves along the second layer whether the second layer is vertical or horizontal. The corrugations are placed in an absorbent structure, such as a diaper or incontinent product, so as to lie parallel to the longitudinal axis of the product.

Body fluids such as urine, menstrual fluid or other fluids are deposited in a localized area on the first fibrous layer in any given area of the absorbent product. The second layer immediately commences its draining and transporting activity to remove the liquid from the localized area. As the liquid front moves horizontally, it also moves vertically, thus gradually being transferred from one transverse fold to another.

BRIEF DESCRIPTION OF THE DRAWINGS

FIG. 1 is a side elevational view of a portion of suitable starting material for the present invention;

FIG. 2 is a side elevational view of the starting material of FIG. 1 after transverse folding has taken place;

FIG. 3 is a perspective view illustrating one embodiment of the present invention;

FIG. 3A is an enlarged cross-sectional view through lines 3A—3A of FIG. 3;

FIG. 4 is a perspective view illustrating another embodiment of the present invention;

DETAILED DESCRIPTION OF THE INVENTION

Figure 5:
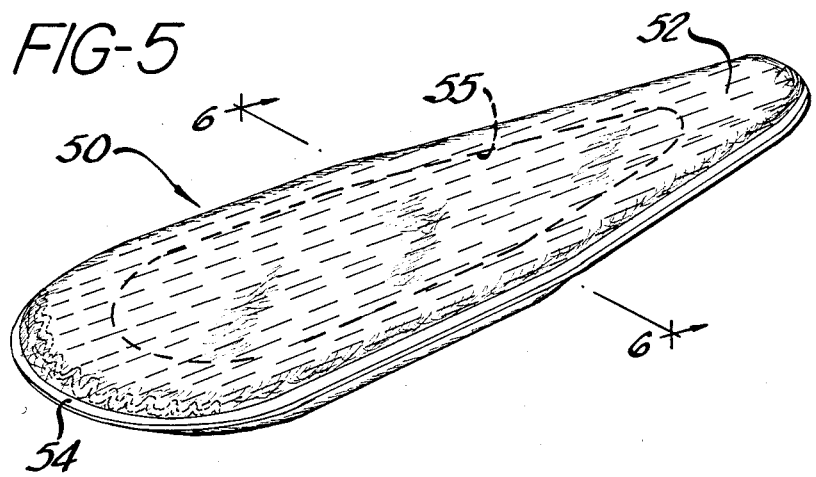
FIG. 5 is a perspective view illustrating still another embodiment of the present invention.

FIG. 1 represents a side elevational view of a segment of starting material 10 depicting a first fibrous layer 12 and a united second layer 14 prior to a transverse folding or corrugation treatment of the starting material 10.

FIG. 2 provides a side elevational view of the starting operation of corrugating the starting material 20. The starting material 20 consists of a nonwoven fibrous web 22, and a second layer 24 of fibers wherein the density is greater than that of the fibrous layer 22.

FIG. 3 is a perspective view of an absorbent product of the present invention. The absorbent product 30 contains a corrugated web 33 and a stabilizing substance 36. The stabilizing substance maintains the starting material in its transversely folded or corrugated form even when the absorbent product 30 becomes wet.

FIG. 3A is a cross-sectional view taken along lines 3A—3A which view has been enlarged. The product 30A contains a nonwoven fibrous web 32A to which has been united a second fibrous layer 34A whose density is greater than the nonwoven fibrous web 32A. This second layer 34A along with the united layer 32A has been corrugated and a stabilizing substance 36A has been applied.

Referring to FIG. 4, a diaper 40 is depicted. A moisture pervious facing 42, such as a nonwoven fabric, provides the diaper surface. A moisture-impervious substance 44 such as polyethylene forms the moisture-proof backing of the diaper. The diaper structure 40 contains an absorbent product 43 sandwiched between the facing 42 and the backing 44. The absorbent product 43 is that described in FIG. 3. The diaper side edges are gathered in the crotch region by elastic members 47. To secure the diaper about the waist of the wearer, tape tabs 49 are provided. The diaper product 40 generally has the absorbent product 43 placed in such a manner that the first fibrous layer is immediately adjacent the facing layer 42 and the corrugations run parallel to the longitudinal axis of the product.

Referring now to FIG. 5, a urinary pad 50 is depicted. The urinary pad 50 has a moisture-permeable facing 52 covering the entire upper surface. Immediately beneath the facing 52 is a liquid barrier 54 which encompasses the entire product except for the opening on the upper surface 55 which lies immediately below the facing 52. The opening 55 permits ingress of fluid.

Figure 6:
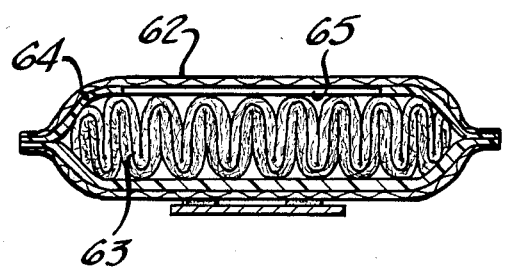
FIG. 6 is an enlarged cross-sectional view through lines 6—6 of FIG. 5.

FIG. 6 is an enlarged cross-sectional view of FIG. 5 taken along lines 6—6. The facing 62 is the layer which is placed against the skin of the wearer. The liquid barrier 64 encompasses the absorbent product 63 except for the opening 65 wherein liquid is permitted to enter. The absorbent product 63 is similar to that depicted in FIG. 3. The first fibrous layer is on the upper surface of the absorbent product 63.

Figure 7:
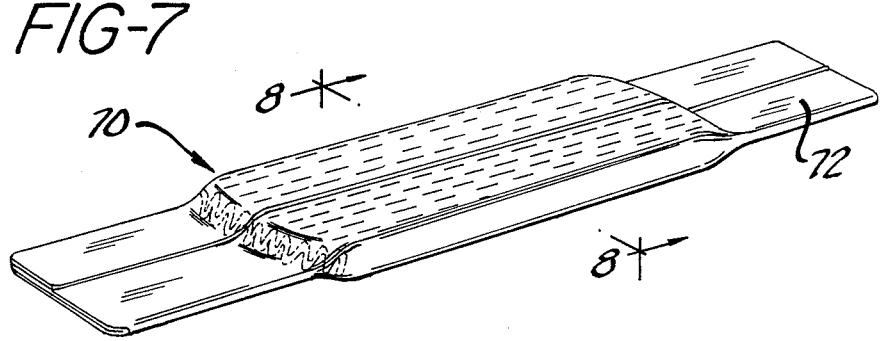
FIG. 7 is a perspective view of a further embodiment of the present invention.

FIG. 7 depicts a sanitary napkin 70 having a fabric overwrap 72 which is liquid permeable.

Figure 8:
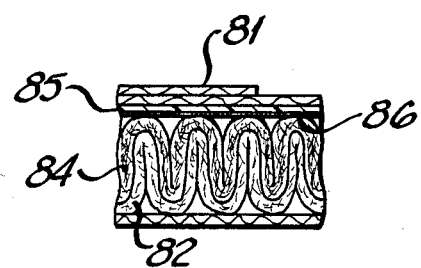
FIG. 8 is a cross-sectional view through lines 8—8 of FIG. 7.

FIG. 8 depicts an enlarged cross-sectional view of FIG. 7 taken along lines 8—8. The liquid permeable overwrap 81 appears with its overlapped portion on the upper surface. Immediately below is a moisture-impermeable barrier which encompasses the sides and bottom of the product. The absorbent product 83 partially encompassed by the liquid barrier 85 and the overwrap 81 has a fibrous layer 82 and a wicking layer 84. The wicking layer 84 is in contact with the stabilizing substance 86 which in turn is in contact with the liquid barrier 85. Thus, the lower surface in the drawing is the side provided for entry of the fluid.

These and other products such as incontinent pads, wound dressings and the like may be made from the absorbent product depicted in FIG. 3.

In the absorbent products of the present invention, the first fibrous layer is on the side which initially receives the liquid void. This initial reception region must be able to accept liquid rapidly and at the same time be able to bear the liquid load, even with body weight pressure applied, until the second layer with its higher capillary pressure drains a substantial portion of the load and begins wicking the liquid away to another part of the product.

What appears to be only a small difference in capillary pressure, is all that is required for the second layer to attract and drain the first fibrous layer of liquid the latter has received. The force causing a liquid to enter a cylindrical capillary is expressed by the equation $$P = (2\nu \cos \theta)/r$$

wherein the force is represented by the capillary pressure and

P is the capillary pressure,
$\nu$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and also increases with narrower capillary radii so that narrower capillaries will draw liquid from wider ones.

The relative wickability between the first fibrous layer and the second layer is affected by both the relative densities of the layers and the relative wettability of the individual fibers in each layer. The individual fibers of the second layer have substantially smaller liquid-fiber contact angles than those of the first fibrous layer overcoming the density difference and providing a significant overall increase in capillary pressure to absorb liquid into the second layer.

The second layer fibers (or particles) and the density of the layer are selected to create a significant difference in capillary pressure from the first fibrous layer.

The first fibrous layer is preferably a fibrous web which is of substantially high loft and which upon dry compression followed by release, has a tendency to return substantially to its original thickness. For instance, fibrous webs formed from synthetic staple fibers such as polyethylene, polypropylene, polyester, nylon, bicomponent fibers, mixtures thereof, and the like are particularly suitable. However, cellulosic fibers such as rayon may be used. Generally the fibers are carded to form a web which is then stabilized if needed. Stabilization may be achieved by heat-through bonding, adhesive bonding, point embossing with heat or adhesive or both, and the like. The stabilizing process is selected according to the fibers used and the process used to form the web. Other suitable procedures for forming a web include carding, wet-laying, spun bonding, laying of melt blown fibers and other known techniques. The fibrous web before corrugation preferably has a dry bulk of at least about 10 cc per gram and a weight less than about 4 ounces per square yard.

In one embodiment a blend of staple polyester fibers with a minor portion of fusible fibers, such as lower melt polyester fibers, are air-laid to form a web. The web is subsequently lightly bonded by passing hot air through the fibers making the fusible fibers tacky so as to stick to each other and the staple fibers, to provide the desired degree of integrity to the web structure.

The second fibrous (or particle) layer is generally comprised of fibers having a lower liquid-contact angle or wherein the layer has a narrower capillary radii. Examples of such fibers include hydrophilic fibers such as rayon fibers, cellulosic fibers, or peat moss, or mixtures thereof, or acrylic fibers, or the like. Cellulosic fibers include wood pulp fibers, cotton linters and the like.

The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton and the like. The fibers, or peat moss, or mixtures thereof are placed in such a way as to form a layer in which the particles are close to one another so as to promote wicking of liquid in the plane of the layer.

The second layer can be preformed and placed next to the first fibrous layer or, the particles (fibers or peat moss or mixtures thereof) can be air-laid or wet-laid onto the first fibrous layer before the transverse folding or corrugating takes place.

Corrugating or transverse folding of the web is provided by known procedures such as that exemplified in U.S. Pat. No. 4,111,733.

After corrugating the two layer material, the corrugated structure is stabilized to prevent the corrugations from pulling apart and flattening out. One method of stabilizing the web is accomplished by using an adhesive binder which may be a latex resin or other known adhesive. A typical way to stabilize the corrugated material is to spray an adhesive on one corrugated surface thereof. Generally the surface selected for the stabilizing is the surface where the second more dense layer is present. The non-stabilized surface is open and available to receive fluids. Another method of stabilizing the web is to add a minor portion of fibers having a lower melting point than the remaining fibers in the layers and subject the corrugated web to temperatures sufficient to melt the minor fibers thereby providing light bonding between the corrugations.

In order for the first fibrous layer to provide the most desired medium for receiving and holding liquid, it is preferred that the fibrous web have a dry bulk of at least about 10 cc per gram and a weight of less than about 4 ounces per square yard prior to corrugation presently from about 1 to about 2 oz. per sq. yd. The web corrugations range from about three to about six or even eight per inch of corrugated web. The corrugated web is generally from about $\frac{1}{4}$ to about 3 inches preferably from about $\frac{1}{2}$ to about one inch thick.

It has been found that using a corrugated web as the provider of void volume to contain body fluids has many advantages. For instance, fibers may be used to form the web that in the non-corrugated web form to do not have enough wet resilience to retain void volume when the web becomes wet. Corrugating of the web provides the highly desirable resilience in the product that is required to initially accept and hold a high volume of fluid. Also it has been found that superabsorbent may be randomly distributed in small or large quantities within the web with surprisingly high utilization of the superabsorbent. It is theorized that the wet resilience of the corrugated web permits the void volume to remain available almost in totality when large quantities of fluid are present in the web. This would permit the superabsorbent to swell, as it captures the liquid, without substantial inhibition.

Examples of methods of preparing the absorbent product of the present invention are as follows. These examples are not intended to be limiting in any way and extensions and modifications thereof without departure from the spirit and scope of the invention will become apparent from these examples.

EXAMPLE I

An absorbing layer is formed of polyester fibers by dry laying the fibers i.e., by air-laying or carding to form a web. Specifically the polyester fibers contain a minor portion, about 10 to 15% by weight, of fusible fibers which soften at a lower temperature than the rest of the fibers. The specific polyester fibers used are identified as Type 676 fibers manufactured and sold by E. I. DuPont Company. Acrylic fibers are deposited onto the polyester web to form a discrete but gently-united layer of acrylic fibers. The two layer flexible longitudinal web is subjected to corrugating in accordance with the procedures set forth in U.S. Pat. No. 4,111,733 and heating to a temperature of about 275° F. for a few seconds. The corrugating provides a final product having a thickness of approximately $\frac{3}{4}$ inch weighs about 13 oz/yd$^2$ and having approximately four corrugations per inch. The corrugations are provided transversely to the web.

EXAMPLE II

Bicomponent fibers consisting of polyester surrounded by polypropylene in a core sheath relationship are air-laid to form a nonwoven web which is heat bonded by subjecting the web to heat for a few seconds at about 275° F. The resulting web is 25 grams per square meter, basis weight. The web is passed beneath a hammermill that deposits chemically treated wood pulp fibers onto the web. Vacuum is applied under the web so as to cause some of the pulp fibers to at least partially migrate into the nonwoven web. The major portion of the wood pulp fibers reside on the surface providing a layer containing wood pulp fibers of 50 grams per square meter. The formed structure is lightly compressed and then corrugated in accordance with the procedure used in Example I. After the web has been corrugated, it is stabilized by spraying an elastomer solution onto one surface of the corrugated web. Preferably, this surface is the surface of the wood pulp fibers. The aqueous dispersion of the elastomer is cured and the product is stabilized. The stabilized corrugated product is ready for use.

EXAMPLE III

A disposable diaper similar to that depicted in FIG. 4 is assembled using a polyethylene backing sheet and a polyester nonwoven fabric as the facing sheet. The absorbent core is provided by a section of the absorbent product of Example I measuring 8 inches wide and 13 inches long. The diaper is assembled by known techniques utilizing hot-melt adhesive to adhere the absorbent core to the backing, and the facing and backing to each other in the side and end margins. The resulting product will contain up to about 200 ml. of urine.

EXAMPLE IV

A urinary pad to be worn by an adult is prepared by utilizing a soft, liquid-impermeable shell which is boat-like in shape. A corrugated web, like that of Example II, is prepared substantially the same except that the web is corrugated to a height of one inch. A section of corrugated web is shaped by cutting it to fit into the shell (see FIG. 5) so that the corrugations run lengthwise. The corrugated web section is placed in the shell with the polyester web side up and a polyester liquid-permeable facing is placed over the corrugated web and adhered to the edge of the shell. Suitable means for adhering the bottom of the shell to the user's under-clothing is provided. When being used, the urinary pad is placed so that the wide portion is at the front of the crotch. The urinary pad will contain up to about 100 ml. of urine.

Other methods for preparing the absorbent product of the present invention may be used.

From the foregoing it will be observed that numerous variations and modifications may be effected without departing from the true spirit and scope of the novel concept of this invention.

What is claimed:

1. An absorbent product comprising a first fibrous layer of synthetic resilient fibers in the form of a nonwoven web and a second layer substantially united to said first layer, said second layer having a higher capillary pressure than said first layer to provide preferential attraction and wicking of liquid in said second layer, said layers being corrugated to provide a corrugated structure, said corrugated structure being stabilized to retain its corrugations when wet.

2. The absorbent structure of claim 1 wherein the nonwoven web is polyester.

3. The absorbent structure of claim 1 wherein the nonwoven web is made from bicomponent fibers.

4. The absorbent structure of claim 1 wherein the second layer is chemically delignified wood pulp fibers.

5. The absorbent structure of claim 1 wherein the second layer is peat moss.

6. The absorbent structure of claim 1 wherein the second layer is acrylic fibers.

7. An absorbent product comprising a first layer and a second layer, said second layer being substantially united to said first layer and substantially coextensive therewith, said first layer comprising a fibrous web of synthetic resilient fibers said web having a dry bulk of at least about 10 cc per gram and a weight less than about 4 ounces per square yard, said second layer comprising frictionally engaged hydrophilic particles selected from the group consisting of cellulosic fibers, peat moss, rayon fibers, acrylic fibers and mixtures thereof, said first and second layers being corrugated and stabilized to retain the corrugated form even when wet.

8. The absorbent product of claim 7 wherein said first fibrous layer is a nonwoven fibrous web.

9. The absorbent product of claim 8 wherein said nonwoven fibrous web is of polyester fibers.

10. The absorbent product of claim 7 wherein said second layer is chemically delignified wood pulp fibers.

11. The absorbent product of claim 7 wherein said second layer is peat moss.

12. The absorbent product of claim 7 wherein said second layer is rayon fibers.

13. A disposable diaper containing an absorbent pad wherein said absorbent pad is an absorbent product comprising a first fibrous layer of synthetic resilient fibers in the form of a nonwoven web and a second layer substantially united to said first layer, said second layer having a higher capillary pressure than said first layer to provide preferential attraction and wicking of liquid in said second layer, said layers being corrugated to provide a corrugated structure, said corrugated structure being stabilized to retain its corrugations when wet.

14. The disposable diaper of claim 13 wherein said absorbent structure is comprised of a first layer nonwoven web of polyester fibers and a second layer of chemically delignified wood pulp fibers.

15. A disposable diaper containing an absorbent pad wherein said absorbent pad is an absorbent structure comprising a first layer and a second layer, said second layer being substantially united to said first layer and substantially coextensive therewith, said first layer comprising a fibrous web of synthetic resilient fibers said web having a dry bulk of at least about 10 cc per gram and a weight less than about 4 ounces per square yard, said second layer comprising frictionally engaged particles selected from the group consisting of cellulosic fibers, peat moss, rayon fibers, acrylic fibers, and mixtures thereof, said first and second layers after being united being corrugated and stabilized to retain the corrugated form.

16. A sanitary napkin comprising an absorbent structure partially encompassed by a liquid barrier with a moisture permeable overwrap, said absorbent structure being an absorbent product comprising a first fibrous layer of synthetic resilient fibers in the form of a nonwoven web and a second layer substantially united to said first layer, said second layer having a higher capillary pressure than said first layer to provide preferential attraction and wicking of liquid in said second layer, said layers being corrugated to provide a corrugated structure, said corrugated structure being stabilized to retain its corrugating when wet.

17. A sanitary napkin containing an absorbent structure, said absorbent structure being an absorbent product comprising a first layer and a second layer, said second layer being substantially united to said first layer and substantially coextensive therewith, said first layer comprising a fibrous web of synthetic resilient fibers said web having a dry bulk of at least about 10 cc per gram and weight less than about 4 ounces per square yard, said second layer comprising frictionally engaged particles selected from the group consisting of cellulosic fibers, peat moss, rayon fibers, acrylic fibers, and mixtures thereof, said first and second layers after being united being corrugated and stabilized to retain the corrugated form.

* * * * *